United States Patent [19]

Kaneko et al.

[11] Patent Number: 5,202,459

[45] Date of Patent: Apr. 13, 1993

[54] PROCESS FOR PRODUCING CYCLOBUTANE DERIVATIVE

[75] Inventors: Chikara Kaneko; Nobuya Katagiri, both of Sendai, Japan

[73] Assignee: Nippon Kayaku Kabushiki Kaisha, Tokyo, Japan

[21] Appl. No.: 598,233

[22] Filed: Oct. 16, 1990

[30] Foreign Application Priority Data

Nov. 7, 1989 [JP] Japan .................................. 1-287810
Jan. 29, 1990 [JP] Japan .................................. 2-016044

[51] Int. Cl.$^5$ .................. C07D 473/00; C07C 215/42
[52] U.S. Cl. .................................. 560/123; 556/401; 556/436; 562/505; 558/433
[58] Field of Search .................. 564/57; 540/203; 549/510; 560/123; 562/505; 556/401, 436; 558/433

[56] References Cited

U.S. PATENT DOCUMENTS

| | | | |
|---|---|---|---|
| 4,514,571 | 4/1985 | Nakai et al. | 564/57 X |
| 4,845,215 | 6/1989 | Shimada | 544/265 |
| 4,892,876 | 7/1989 | Hoshino | 514/265 |
| 4,960,910 | 8/1990 | Kato | 549/510 |
| 4,988,688 | 1/1991 | Kester et al. | 564/57 X |
| 4,992,368 | 2/1991 | Saito | 435/88 |
| 5,028,598 | 7/1991 | Kurabayashi | 514/18 |
| 5,041,447 | 8/1991 | Saito | 435/88 |

FOREIGN PATENT DOCUMENTS 0291917 11/1988 European Pat. Off. .
0322854 2/1989 European Pat. Off. .
0334250 9/1989 European Pat. Off. .
0366059 2/1990 European Pat. Off. .
0358154 3/1990 European Pat. Off. .
3-504728 10/1991 Japan .

OTHER PUBLICATIONS

Antiviral Research, vol. 13, No. 1, Jan. 1990, pp. 41–52, Elsevier Science Publishers B.V. (Biomedical Division):A. K. Field, et al.
Tetrahedron Letters, 29, 4739–4742, 1988.
Kurabayashi et al, "Preparation of novel oxetane, etc." CA115: 136655t (1991).
Antimicrobial Agents and Chemotherapy, May 1989, pp. 773–775.

The Journal of Antibiotics, vol. 17, No. 4, 644–646 (1989).
XXIX Interscience Conference on Antimicrobial Agents and Chemotherapy 17–20 Sep., 1989, "Biochemical Activity of the New Antiviral SQ 32,829".
XXIX Interscience Conference on Antimicrobial Agents and Chemotherapy 17–20 Sep., 1989, "In vitro Activity of SQ-32,829, A New Nucleoside-Analog Antiviral Agent."
XXIX Interscience Conference on Antimicrobial Agents and Chemotherapy 17–20 Sep., 1989, "Efficacy of SQ 33,054 [(±)-BHCG] in Herpes Virus Infections in Mice".

Primary Examiner—Arthur C. Prescott
Attorney, Agent, or Firm—Nields & Lemack

[57] ABSTRACT

The present invention relates to a process for producing cyclobutane derivatives represented by general formula (28):

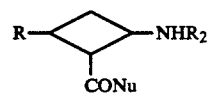

(28)

(wherein R represents a substituent; $R_2$ represents an electron attracting group and Nu represents a substituent corresponding to nucleophilic reagent), by reacting a compound represented by general formula (27):

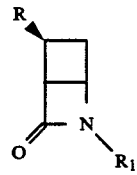

(27)

(wherein R has the same significance as defined above and $R_1$ represents an electron attracting group) with nucleophilic reagents $Nu^\ominus$ in a solvent.

The compounds of formula (28) are useful as intermediates for synthesis of, for example, 9-[2,3-bis(hydroxymethyl)cyclobutan-1-yl]guanine which is expected to be useful as an antiviral agent.

12 Claims, No Drawings

PROCESS FOR PRODUCING CYCLOBUTANE DERIVATIVE

FIELD OF THE INVENTION

The present invention relates to a novel process for producing cyclobutane derivatives useful as intermediates for synthesis of 9-[2,3-bis(hydroxymethyl)cyclobutane-1-yl]guanine represented by formula (I) described below, which is expectedly useful as, e.g., an antiviral agent.

BACKGROUND OF THE INVENTION

Oxetanocins are antibiotics which were recently found (U.S. Pat. No. 4,743,689):

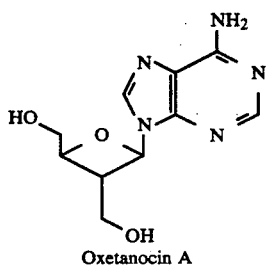

Oxetanocin A and are nucleosides showing anti-tumor and anti-viral activities which contain as sugar the oxetan ring in place of ribose.

Physiological activities of cyclobutane derivatives in which carbon has been substituted for oxygen in the oxetan ring of oxetanocin have attracted the present inventors' attention. The present invention is to provide a novel process for producing such cyclobutane derivatives as intermediates for synthesis.

PRIOR ART

9-[2,3-Bis(hydroxymethyl)cyclobutane-1-yl]-guanine shown by the formula (I) is known and disclosed in EP-A-2-0335355 and is synthesized by the following reaction schemes, using diethyl fumarate and ketene diethyl acetal as starting materials:

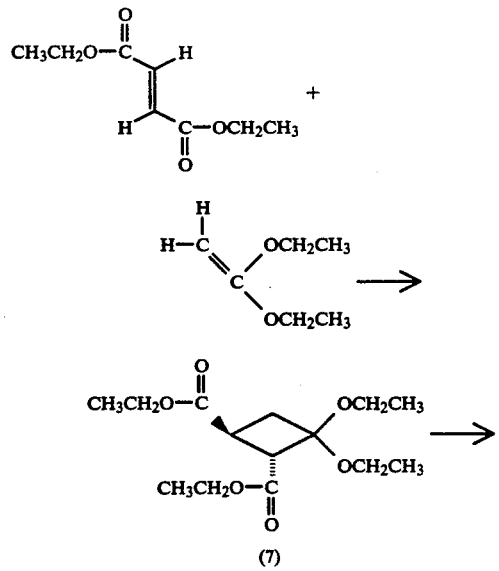

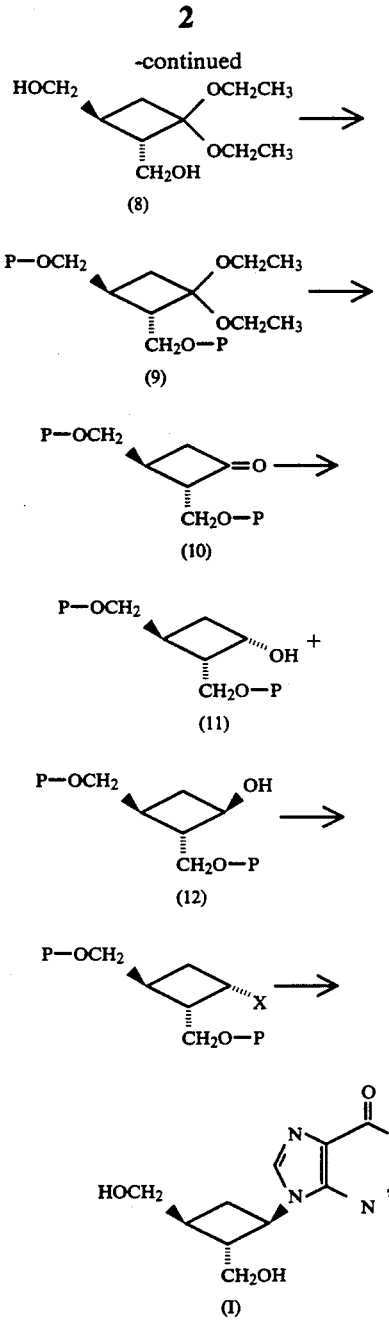

SUMMARY OF THE INVENTION

The present invention is directed to a process for producing a cyclobutane derivative represented by general formula (28):

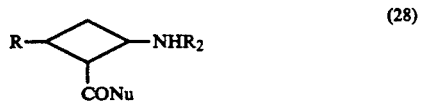

(wherein R represents a substituent; $R_2$ represents an electron attracting group and Nu represents a substituent corresponding to nucleophilic reagent) which comprises reacting a compound represented by general formula (27):

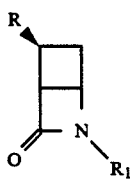

(27)

[wherein R has the same significance as defined above and R₁ represents an electron attracting group] with a nucelophilic reagent Nu⁻ in a solvent.

DETAILED DESCRIPTION OF THE INVENTION

In the general formulae (27) and (28) described above, R represents a substituent and is not particularly limited. The substituent may be, e.g., an alkyl group, a hydroxy group which may be protected, a hydroxymethyl group which may be protected, etc. Examples of the alkyl group include an alkyl group having 1 to 8 carbon atoms such as methyl group, ethyl group, t-butyl group, phenyl alkyl group, etc. As the protective group for the hydroxy group which may be protected and for the hydroxymethyl group which may be protected, any protective group may be used without restriction so long as it is conventionally used as a protective group. Examples of such protective groups include: (1) ester type protective groups such as acyl groups, e.g., acetyl group, benzoyl group, etc.; carbamoyl groups such as dimethylcarbamoyl group, diphenylcarbamoyl group, etc.; and (2) ether type protective groups such as silyl protective groups, e.g., trimethylsilyl group, t-butyldiphenylsilyl group, t-butyldimethylsilyl group, etc.; ($C_1$-$C_4$)-alkoxy-($C_1$-$C_4$)-alkyl groups such as methoxymethyl group, etc.; or substituted methyl group such as benzyl group, etc. R₁ is an electron attracting group. Examples of the electron attracting group are a carbamoyl group shown by formula: —CONHR' (wherein R' is a substituent) and a group shown by formula: —COR" (wherein R" is a substituent). R' is not particularly limited and exemplified by hydrogen, an acyl group such as chloroacetyl group; an alkyl group such as methyl group; an aryl group such as phenyl group, etc. Examples of R" include an alkyl group such as methyl group, especially a $C_1$ to $C_5$ lower alkyl group, an alkoxy group such as methoxy group, ethoxy group, especially a $C_1$ to $C_5$ lower alkoxy group, and a phenyl group, etc. Specific examples of R₁ include carbamoyl group, chloroacetylcarbamoyl group, ethoxycarbonyl group, etc. As the nucleophilic reagent Nu⁻, there are lower ($C_1$ to $C_5$) alkoxide ions such as —OCH₃⁻, —OC₂H₅⁻, etc ; anions such as OH⁻, CN⁻, NH₂⁻, OCOCH₃⁻, etc. R₂ in formula (28) is an electron attracting group and exemplified by the same groups as for R₁ described above. Examples of the substituent Nu corresponding to nucleophilic reagent Nu⁻ are an alkoxy group, hydroxy group, cyano group, amino group, substituted amino group such as methyl amino group, acetoxy group, etc.

The process of the present invention is specifically described below. The compound of formula (27) is reacted with the nucleophilic reagent Nu⁻ at −30° to 100° C., preferably −10° to 50° C. for a minute to 48 hours, preferably a minute to 10 hours, in a solvent to give the compound of formula (28).

Examples of compounds which permit to release the nucleophilic reagent Nu⁻ include an alkali metal alkoxide such as sodium methoxide, potassium ethoxide, etc.; a metal amide such as sodium amide, etc.; ammonia, sodium cyanide, sodium acetate, sodium hydroxide, etc. Where alcohols as the nucleophilic reagent are used, it is preferred to use trialkylamines such as triethylamine, etc. or borohydride compounds such as sodium borohydride, calcium borohydride, etc. in combination.

As the solvent, alcohols, for example, methanol, ethanol, etc., ethers such as dioxane, etc. are preferably used.

A ratio of the nucleophilic reagent Nu⁻ based on the compound of formula (27) may be approximately 0.5 to 10-fold mols, preferably 1 to 3-fold mols, when expressed by a ratio of the reagent for releasing the nucleophilic reagent.

Further in the process of the present invention, the compound of formula (28) which has a different steric configuration can be obtained depending upon kind of the reagent used for releasing the nucleophilic reagent. That is, when the compound of formula (27) is reacted with a borohydride compound in an alcohol, the β-lactam ring is cleaved in such a state that the steric configuration is still maintained to give (1β, 2β, 3β) compound represented by formula (28a) below:

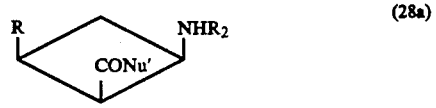

(28a)

(wherein R and R₂ have the same significances as described above and Nu' represents an alkoxy group). The reaction may be carried out at −30° C. to 100° C. for approximately 1 to 48 hours. In this reaction, the following compound shown by formula (29a):

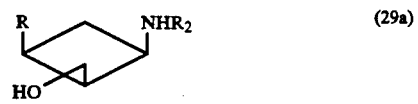

(29a)

wherein the —CONu' group in the compound of formula (28a) is reduced, is also obtained.

Also when the compound (27) is reacted with an alcohol such as methanol, etc. and a catalytic amount of trialkylamine at −30° C. to 200° C. for about 1 to about 48 hours, the (1β, 2β, 3β) compound represented by formula (28a) described above can be obtained. In this case, the compound shown by formula (29a) described above is not obtained.

On the other hand, where an alkali metal alkoxide is used as the compound for releasing the nucleophilic reagent Nu⁻, (1β, 2β, 3β) compound represented by formula (28b) below:

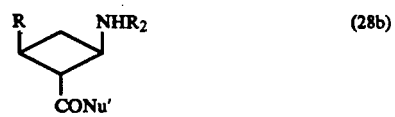

(28b)

wherein R, R₂ and Nu' have the same significances as described above) can be obtained.

An ratio of the alkali metal alkoxide may be about 0.1 to about 10-fold mols, based on the compound of formula (27). As the solvent, there may be preferably used inert solvents such as alcohols, e.g., methanol, etc.; ethers such as tetrahydrofuran, etc.; and hydrocarbons and the like. The reaction is completed at $-30°$ to $100°$ C. for about 1 minutes to about 48 hours. When the $(1\beta, 2\beta, 3\beta)$ compound shown by formula (28a) is reacted with the alkali metal alkoxide described above under the same conditions as described above, epimerization of the —CONu group at the 2-position occurs to give $(1\beta, 2\beta, 3\beta)$ compound shown by (28b). The compound of formula (28b) is preferable as an intermediate for synthesis of cyclobutane ring-containing compounds having the same steric configuration as oxetanocin.

Further where $NaNH_2$ or $NH_3$ is used as the compound for releasing the nucleophilic reagent, compounds of formula (28) wherein Nu is $NH_2$ are obtained; where NaCN or KCN is used, compounds of formula (28) wherein Nu is CN are obtained; where $CH_3COONa$ is used, compounds of formula (28) wherein Nu is $COCH_3$ are obtained; and where NaOH is used, compounds of formula (28) wherein Nu is OH are obtained.

Throughout the present specification, when relative steric configuration of compounds is viewed from the cyclobutane ring as a flat plane, a substituent located at the lower part of the flat plane (one plane) is expressed as $\alpha$ and a substituent located at the upper part of the flat plane (another plane) is expressed as $\beta$.

In the reaction of the present invention, the cleavage of the $\beta$-lactam ring does not occur even when compounds of formula (27) wherein $R_1$ is replaced with hydrogen atom is treated in a manner similar to the present invention. This suggests that a carbamoyl group, an acyl group or a group functionally equivalent thereto (electron attracting group) in $R_1$ would be necessary for the cleavage reaction.

The compounds of formula (27) which are the starting material of the present invention can be prepared by the following reaction scheme:

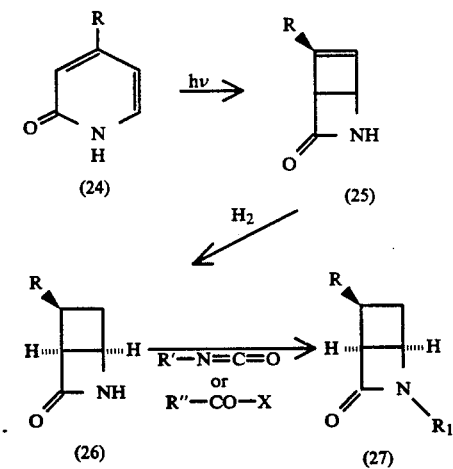

(wherein R, $R_1$, R' and R" have the same significances as described above, and X represents a reactive group). That is, the compounds of formula (27) can be obtained by firstly subjecting 2-pyridones shown by formula (24) to photoreaction, then reducing the resulting photopyridones of formula (25), and finally reacting the resulting bicyclo compounds shown by formula (26) with isocyanates shown by formula: R'—N=C=O or compounds shown by formula: R"—CO—X.

The photoreaction at the first step may be effected by exposing the 2-pyridones of formula (24) to light having a wavelength of not shorter than 150 nm, preferably not shorter than 300 nm in an output of 10 to 100,000 w, preferably 100 to 10,000 W for 1 to 240 hours, preferably 1 to 48 hours, at $-30°$ to $100°$ C., preferably $-10°$ to $50°$ C., in an inert solvent in the reaction such as acetonitrile, etc. As a light source, there may be used, for example, a high pressure mercury lamp with a pyrex filter. For the next reduction, catalytic reduction is preferred and the reduction may be performed by reacting the photopyridones of formula (25) with hydrogen for about 0.1 to about 10 hours in an inert solvent in the reaction such as alcohol, for example, methanol, etc. in the presence of a catalyst such as palladium-carbon, etc. In this reaction addition of hydrogen occurs from the exo site at which steric hindrance is less and hence, only the compounds of formula (26) can be stereo selectively obtained.

The reaction for preparing the compounds of formula (27) from the compounds of formula (26) can be performed at $-30°$ to $100°$ C., preferably $-10°$ to $30°$ C., for about 0.5 to about 48 hours, preferably 1 to 24 hours in an inert solvent such as benzene, chloroform, tetrahydrofuran or the like, using 1 to 10-fold mols, preferably 1.0 to 3-fold mols of the isocyanates or acylating agents based on the bicyclo compounds of formula (26).

Examples of the isocyanates represented by formula: R'—N=C=O include chloroacetyl isocyanate, an alkyl isocyanate, an aryl isocyanate, etc. As R' in the above formula: R'—N=C=O, there are, for example, an acyl group such as chloroacetyl group etc., an alkyl group having 1 to 5 carbon atoms such as methyl group, ethyl group, etc., an aryl group such as phenyl group, etc. Further as reactive derivatives of the compounds shown by R"—CO—X, there are, for example, ethyl chloroformate, acetic anhydride, ethyl chlorocarbonate, etc.

From the compounds of formula (28) described above, compounds represented by formula (29):

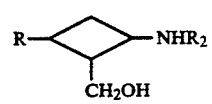

(29)

(wherein R and $R_2$ have the same significances as described above) can be obtained. That is, the compounds of formula (29) can be obtained by reducing the compounds of formula (28) in an alcohol solvent such as methanol, ethanol, etc., at $-30°$ to $150°$ C., preferably $0°$ to $80°$ C., for 0.5 to 72 hours, preferably 1 to 48 hours, in the presence of a reducing agent such as sodium borohydride, calcium borohydride, etc., whereby the steric configuration of the starting material can be still maintained. In the case of using, for example, the compounds of formula (28b) as the starting material, compounds represented by formula (29b) described below:

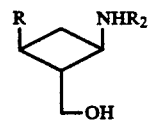

(29b)

(wherein R and $R_2$ have the same significances as described above) which are the $(1\beta, 2\beta, 3\beta)$ form of the compounds of formula (29).

In the compounds of formula (29b), compounds wherein R is a hydroxymethyl group which may be optionally protected are desirable as intermediates for synthesis of nucleosides containing the cyclobutane ring of oxetanocin type.

When the compounds of formula (29) wherein $R_2$ is a carbamoyl group are decomposed by diazotization, compounds represented by formula (29-H):

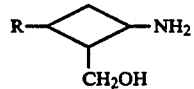
(29-H)

can be obtained; in this case, the steric configuration possessed by the starting material is still maintained.

The diazotization can be carried out by reacting the compounds of formula (29) with a diazotizing agent such as sodium nitrite, etc. at $-30°$ to $50°$ C., preferably $-10°$ C. to $30°$ C. for 1 to 24 hours, preferably 1 to 5 hours, in an acidic solvent such as a hydrochloric acid aqueous solution, etc.

From the compounds of formula (29-H) described above, various carbon ring oxetanocins can be obtained. Using, for example, the (1β, 2β, 3β) compounds represented by formula (29b-H) described below:

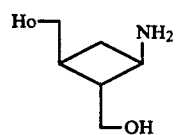
(29b-H)

one example of its synthetic routes is shown below (Nucleic Acids Research Symposium Series, No. 21, 1989):

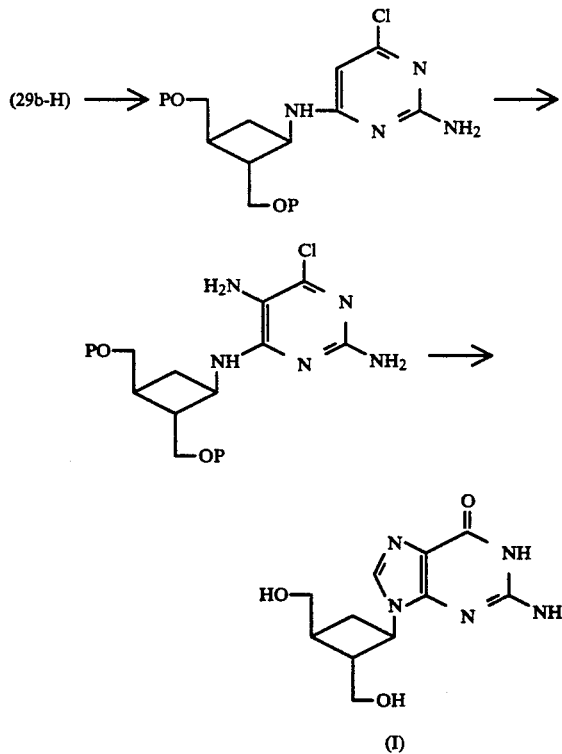

(wherein P represents cyclohexylcarbonyl group).

Hereafter the present invention is described in more detail with reference to the examples below but is not deemed to be limited to these examples.

EXAMPLE 1

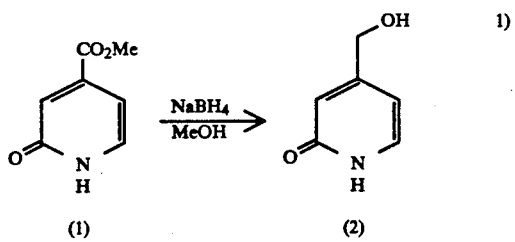

After Compound (1) (1.18 g, 7.7 mmols) was suspended in methanol (30 ml), $NaBH_4$ (2.91 g, 77 mmols) was added to the suspension by small portions at room temperature with stirring. Upon the addition of $NaBH_4$, heat generated but the reaction was carried out without cooling. At the end of the reaction, the reaction mixture was neutralized with acetic acid-methanol (1:1) followed by concentration under reduced pressure. The residue was chromatographed on silica gel with ethyl acetate to recover 320 mg of the starting material. Next, the column was eluted with ethyl acetate-methanol (3:1) to give 0.577 g (60%) of the product (2).

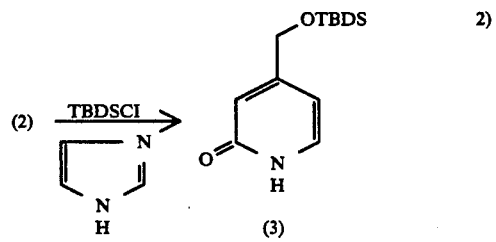

After Compound (2) (360 mg, 2.88 mmols) was dissolved in N,N-dimethyl formamide (6 ml), t-butyldimethylsilyl chloride (521 mg, 3.45 mmols) and imidazole (588 mg, 8.64 mmols) were added to the solution. The mixture was allowed to stand overnight. At the end of the reaction, the reaction mixture was poured onto ice water followed by extraction with ether. The ethereal layer was dried and concentrated. The resulting crystals were recrystallized from ether-hexane to give 400 mg of Compound (3) showing a melting point of 126° to 127° C. as colorless needles.

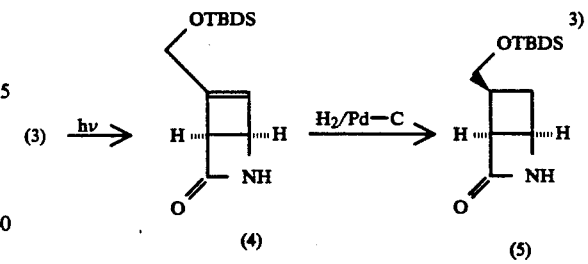

After Compound (3) (400 mg) was dissolved in acetonitrile (300 ml), the solution was exposed to a light for 6 hours using a high pressure mercury lamp (400 W, pyrex filter) while cooling with a mixture of sodium chloride and ice. The solvent was distilled off under reduced pressure to give Compound (4). This Compound (4) without purification was dissolved in methanol (25 ml). After 100 mg of 5% Pd-C was added to the solution, the mixture was shaken for 2 hours in a hydrogen atmosphere. The catalyst was filtered off and the filtrate was concentrated under reduced pressure. The residue was chromatographed on silica gel with ethyl acetate-hexane (6:4) to give 286 mg of the product (5).

Compound 5: m.p. 48°-50° C. (hexane, colorless leaflets)

Elemental analysis ($C_{12}H_{23}O_2NSi$)
Calcd.: C, 59.71%; H, 9.61%; N, 5.80%
Found : C, 59.84%; H, 9.59%; N, 5.80%

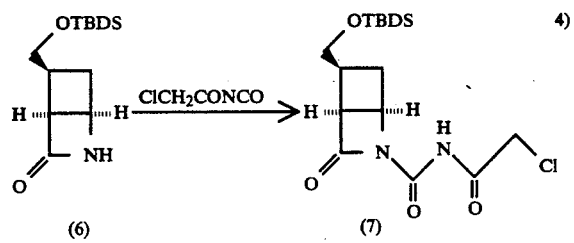

After Compound (6) (280 mg, 1.16 mmol) was dissolved in dry benzene (5 ml), chloroacetyl isocyanate (167 mg, 1.39 mmol) was added to the solution under ice cooling. The mixture was allowed to stand at room temperature overnight and the solvent was then distilled off under reduced pressure. The residue was chromatographed on silica gel with hexane-ethyl acetate (4:1) to give 360 mg of the oily product (7).

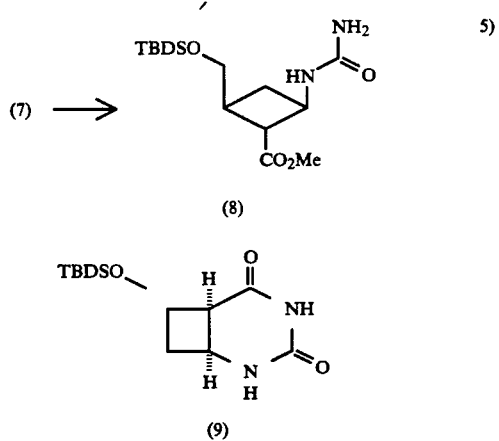

Compound (7) (200 mg, 0.6 mmol) was added to a sodium methoxide-methanol solution under ice cooling. The mixture was allowed to stand at room temperature overnight. At the end of the reaction, acetic acid (120 mg, 2 mmols)-methanol (1 ml) was added to neutralize the reaction mixture. After the mixture was concentrated under reduced pressure, the residue was chromatographed on silica gel with hexane-ethyl acetate (1:3). Compound (9) (41 mg, 24%) was initially eluted and then 119 mg (62%) of the product (8) was obtained.

Compound 8: m.p. 74°-76° C. (ether)
Compound 9: m.p. sublimated at about 120° C. (recrystallized from ether)

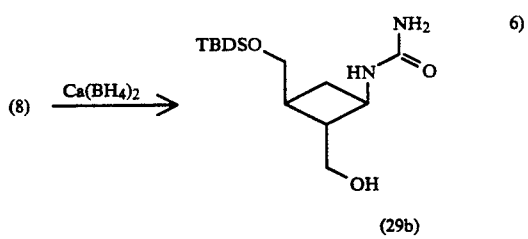

Compound (8) (42 mg, 0.133 mmol) was added at −10° C. to a solution of calcium borohydride in ethanol [prepared by reacting NaBH$_4$ (50 mg)-EtOH (3 ml) with calcium chloride (73.8 mg)-EtoH (3 ml) at −10° C.]. The mixture was allowed to stand at room temperature for 2 days and the solvent was then distilled off under reduced pressure. The residue was again dissolved in a small amount of ethanol and the solution was chromatographed on silica gel with ethyl acetate-methanol (5:1) to give 30 mg (78%) of the product (29b).

Compound (29b): m.p. 142°-143° C. (ether)

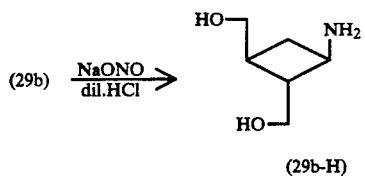

After 1.7 g (6 mmols) of Compound (29b) was dissolved in a 10% HCl aqueous solution (75 ml) while stirring under ice cooling, NaNO$_2$ (750 mg) was added to the solution by small portions. Stirring was continued for about 3 hours under ice cooling. After completion of the reaction, the reaction mixture was neutralized with 10% Na$_2$CO$_3$ aqueous solution under ice cooling. The solvent was removed under reduced pressure. The resulting residue was distilled under reduced pressure to give 330 mg (42%) of (±) (1β, 2β, 3β)-1-amino-2,3-bis(-hydroxymethyl)cyclobutane (29b-H) (b.p., 210° C./0.2 mmHg) as light yellow oil.

NMR (200 MHz, DMSO-d$_6$) δ: 1.72 (1H, apparent q, J=9 Hz), 1.86-2.32 (3H, m) 3.34 (1H, apparent q, J=8 Hz) 3.42 (2H, d, J=5.5 Hz) 3.51 (2H, d, J=5.1 Hz) 4.70 (2H, brs) 7.55 (2H, brs)

IR (KBr)cm$^{-1}$: 3350, 1610, 1500, 1010

EXAMPLE 2

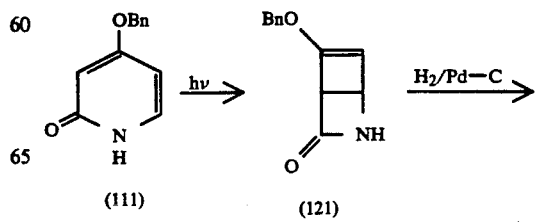

-continued

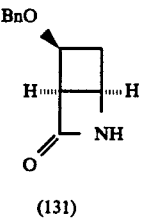

(wherein Bn represents benzyl).

1) After Compound (111) (1.97 g) was dissolved in acetonitrile (700 ml), the solution was exposed to light for 4 hours in an argon flow under ice cooling while stirring, using a high pressure mercury lamp of 1 kw through pyrex filter. The solvent was distilled off below 30° C. under reduced pressure. The residue was washed with ether to give 1.90 g (96%) of the product 121).

2) After Compound (121) (1.88 g) was dissolved in methanol (80 ml), 5% Pd-C (200 mg) was added to the solution. The mixture was catalytically reduced at normal temperature under normal pressure. After one hour, hydrogen absorption was completed. Thereafter the catalyst was filtered off and the filtrate was distilled off under reduced pressure to give 1.7 g (90%) of the product (131).

Compound (131) : m.p. 102°-103° C. (hexane-acetone), colorless needles

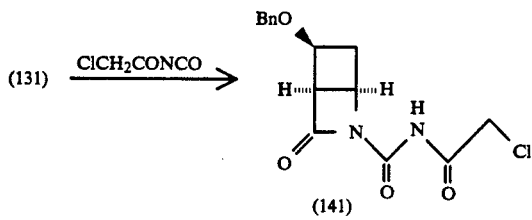

After Compound (131) (930 mg, 4.6 mmols) was dissolved in dry benzene, chloroacetyl isocyanate (825 mg, 6.9 mmols) was added to the solution at room temperature while stirring. The mixture was allowed to stand at room temperature overnight and the solvent was distilled off under reduced pressure. A small amount of ethanol was added to the residue and the mixture was again concentrated to give crystalline Compound (141) quantitatively.

Compound (141): m.p. 70°-71° C. (Et₂O)
Elemental analysis (C₁₅H₁₅N₂O₄Cl)
Calcd.: C, 55.89%; H, 4.69%; N, 8.70%; Cl, 10.86%;
Found: C, 55.74%; H, 4.61%; N, 8.60%; Cl, 10.67%;

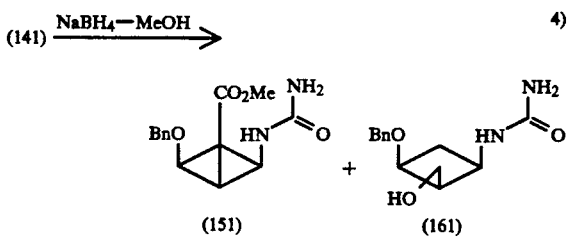

After Compound (141) (70 mg, 0.22 mmol) was dissolved in dry methanol (1 ml), sodium borohydride (41 mg, 1.10 mmol) was added under ice cooling to the solution by small portions while stirring. After twenty minutes, the temperature was elevated to room temperature and the mixture was stirred at room temperature overnight. The reaction solution was neutralized with acetic acid:methanol = 1:1 and then concentrated. The residue was dissolved in ethyl acetate and the solution was chromatographed on silica gel with ethyl acetate:hexane = 1:1 and then with ethyl acetate. Compound (151) (20 mg, 33%) was obtained at the initial stage and Compound (161) (10 mg, 18%) was then obtained.

Compound (151): m.p. 138°-140° C. (ethyl acetate)
Compound (161): m.p. 109°-111° C. (ethyl acetate)

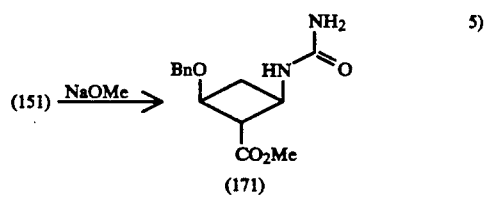

After Compound (151) (200 mg, 0.72 mmol) was dissolved in dry methanol (10 ml), a solution of sodium (33 mg, 1.44 mmol) in dry methanol (10 ml) was added to the solution by small portions at room temperature, while stirring. The reaction was continued overnight. The reaction solution was neutralized with acetic acid:methanol = 1:1. After methanol was distilled off, the residue was washed with water and then extracted with chloroform. The extract was dried over sodium sulfate. The solvent was distilled off under reduced pressure to give the product (171) quantitatively.

Compound (171): m.p. 123°-125° C. (CHCl₃-hexane)
Elemental analysis (C₁₄H₁₈N₂O₄)
Calcd.: C, 60.04%; H, 6.52%; N, 10.07%;
Found : C, 60.43%, H, 6.51%; N, 10.14%;

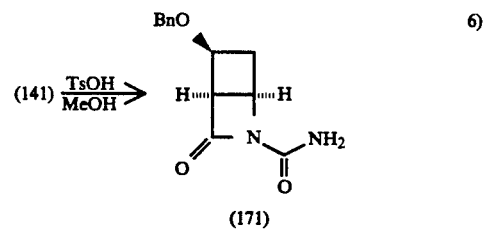

After Compound (141) (120 mg, 0.37 mmol) was dissolved in methanol (2 ml), TsOH (10 mg) was added to the solution. The mixture was stirred at room temperature. Where the reaction did not proceed, the mixture was heated at 60° C. for 3 hours. For removing TsOH from the reaction solution, the reaction solution was washed with water and extracted with chloroform. The extract was dried over sodium sulfate. The solvent was distilled off under reduced pressure to give Compound (171) (73 mg, 80%).

m.p. 143°-145° C. (hexane-acetone)
Elemental analysis (C₁₃H₁₄N₂O₃)
Calcd.: C, 63.39%; H, 5.73%; N, 11.38%;
Found : C, 63.26%; H, 5.94%; N, 11.24%;

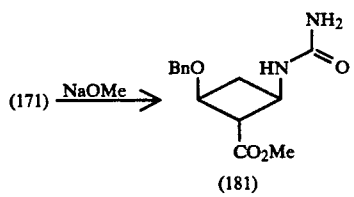

7)

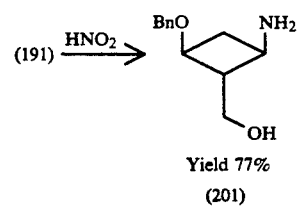

10)

After Compound (171) (173 mg, 0.3 mmol) was dissolved in dry methanol (5 ml), a solution of sodium (14 mg, 0.6 mmol) in methanol (5 ml) was added to the solution by small portions at room temperature while stirring. The mixture was reacted overnight in this state. After the reaction solution was neutralized with acetic acid:methanol=1:1, the solvent was distilled off under reduced pressure. The residue was washed with water and extracted with chloroform followed by drying over sodium sulfate. The solvent was distilled off under reduced pressure to give the product (181) quantitatively.

After Compound (191) (50 mg, 0.2 mmol) was dissolved in a 10% hydrochloric acid aqueous solution (2.5 ml), sodium nitrite (25 mg) was added to the solution by small portions under ice cooling while stirring. When the ice cooling was continued for 2 hours in this state, the starting material was disappeared. The reaction solution was neutralized with sodium carbonate under ice cooling, washed with water, and then extracted with ethyl acetate. After drying over sodium sulfate, the solvent was distilled off to give the product (201) (32 mg, 77%).

8)

EXAMPLE 3

After Compound (141) (200 mg, 0.62 mmol) was dissolved in dry methanol (5 ml), a solution of sodium (22 mg, 0.96 mmol) in methanol (5 ml) was added to the solution by small portions at room temperature while stirring. After eight hours, the starting material disappeared but the reaction was continued overnight in this state. After the reaction solution was neutralized with acetic acid:methanol=1:1, the solvent was concentrated. The concentrate was washed with water and extracted with chloroform followed by drying over sodium sulfate. The solvent was distilled off under reduced pressure to give the product (181) quantitatively.

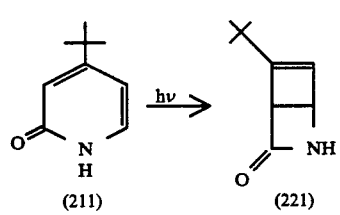

1)

After Compound (211) (450 mg, 3.0 mmols) was dissolved in acetonitrile, the solution was exposed to a light in an argon flow under ice cooling, using a high pressure mercury lamp of 1 kw through a pyrex filter. After thirty minutes, the starting material was disappeared. The solvent was distilled off below 30° C. to give the product (221) (441 mg, 98%).

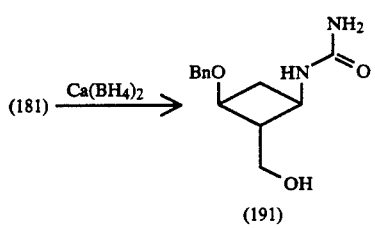

9)

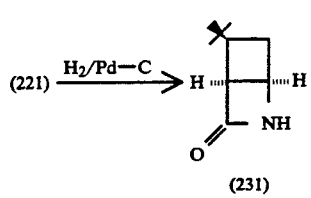

2)

After calcium chloride (600 mg, 5.4 mmols) was dissolved in ethanol (30 ml), a solution of sodium borohydride (400 mg, 10.8 mmols) in ethanol (20 ml) was added to the solution by small portions while stirring under cooling with a mixture of sodium chloride and ice. The mixture was reacted for 30 minutes in this state. A solution of Compound (181) (600 mg, 2.16 mmols) in ethanol (25 ml) was added dropwise to the previous solution. After completion of the dropwise addition, the temperature was elevated to room temperature and the reaction was continued. The reaction solution was concentrated, washed with water and then extracted with ethyl acetate. After drying over sodium sulfate, the solvent was distilled off to give the product (191) (532 mg, 99%).

m.p. 125°-127° C. (chloroform)
Elemental analysis ($C_{13}H_{18}N_2O_3$)
Calcd.: C, 62.38%; H, 7.25%; N, 11.20%;
Found : C, 62.64%; H, 7.23%; N, 11.28%;

After Compound (221) (440 mg, 2.9 mmols) was dissolved in methanol (15 ml), 5% Pd-C (91 mg) was added to the solution followed by catalytic reduction at normal temperature under normal pressure. After one hour, hydrogen absorption was terminated. The catalyst was filtered off and the filtrate was then concentrated. The concentrate was dissolved in a small quantity of ethyl acetate. The solution was subjected to silica gel column chromatography. The column was eluted with ethyl acetate:hexane=1:1 to give the product (231) (390 mg, 88%).

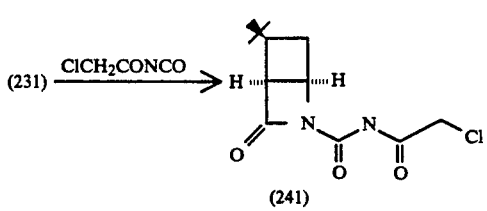

After Compound (231) (390 mg, 2.5 mmols) was dissolved in dry benzene (10 ml), chloroacetyl isocyanate (432 mg, 3.8 mmols) was dropwise added to the solution at room temperature while stirring. After two hours, the starting material was disappeared. The solvent was distilled off under reduced pressure to give the product (241) qnantitatively.

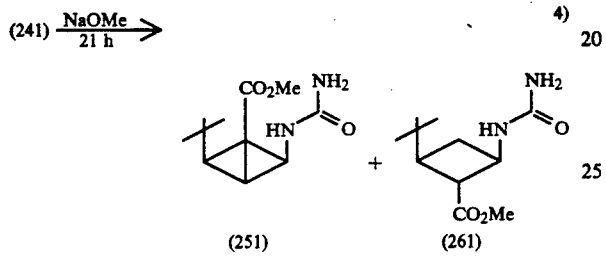

After Compound (241) (860 mg, 3.16 mmols) was dissolved in dry methanol (15 ml), a solution of sodium (145 mg, 6.32 mmols) in methanol (10 ml) was added dropwise to the solution at room temperature while stirring. The reaction was continued overnight. The reaction solution was neutralized with acetic acid:methanol=1:1. After the reaction solution was concentrated, the concentrate was washed with water and then extracted with chloroform. After the extract was dried over sodium sulfate, the solvent was distilled off under reduced pressure. The residue was chromatographed on silica gel with ethyl acetate:hexane=5:1 and then with ethyl acetate. Compound (251) (342 mg, 48%) was initially eluted and Compound (261) (158 mg, 22%) was then obtained.

Compound (261): m.p. 126°–127° C. (benzene)
Elemental analysis ($C_{11}H_{20}N_2O_3$)
Calcd.: C, 57.86%; H, 8.83%; N, 12.18%;
Found : C, 58.10%; H, 8.83%; N, 12.17%;

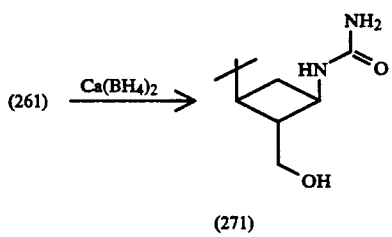

After calcium chloride (122 mg, 1.10 mmol) was dissolved in ethanol (8 ml), a solution of sodium borohydride (81 mg, 2.15 mmols) in ethanol (4 ml) was added to the solution by small portions while stirring under cooling with a mixture of sodium chloride and ice. The mixture was reacted for 30 minutes in this state. A solution of Compound (261) (100 mg, 0.43 mmol) in ethanol (6 ml) was dropwise added to the previous solution. After completion of the addition, the temperature was elevated to room temperature and the reaction was continued overnight. The reaction solution was concentrated. The concentrate was then washed with water and extracted with chloroform. After drying over sodium sulfate, the solvent was distilled off under reduced pressure to give the product (271) (60 mg, 66%).

m.p. 141°–143° C. (ethyl acetate)
Elemental analysis ($C_{10}H_{20}N_2O_2$)
Calcd.: C, 59.97%; H, 10.07%; N, 13.99%;
Found : C, 60.06%; H, 10.09%; N, 13.80%;

EXAMPLE 4

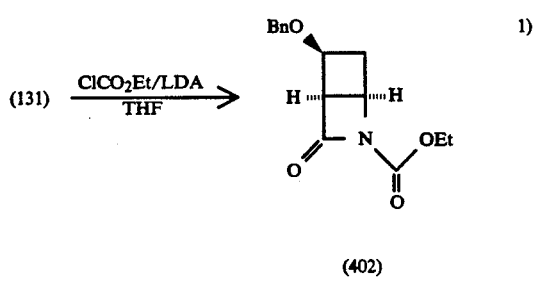

A solution of n-butyl lithium (1.6M in hexane) (1.25 ml, 2 mmols) was added to a solution of diisopropylamine (202 mg, 2 mmols) in tetrahydrofuran (5 ml) at −78° C. and the mixture was stirred for thirty minutes. A solution of compound (131) (203 mg, 1 mmol) in tetrahydrofuran (5 ml) was dropwise added to the mixture and the mixture was stirred for 30 minutes. A solution of ethyl chlorocarbonate (220 mg, 2 mmols) in tetrahydrofuran (5 ml) was dropwise added to the mixture and then the mixture was stirred at −78° C. for 3 hours. Finally, the temperature was gradually raised to room temperature and saturated aqueous ammonium chloride solution (5 ml) was added to the reaction mixture followed by vigorous stirring for 30 minutes. The reaction mixture was extracted with ethyl acetate and the extract was dried over sodium sulfate.

The solvent was distilled off and the residue was chromatographed on silica gel (20 g) with ethyl acetate to give the product (402) (239 mg, 87%).

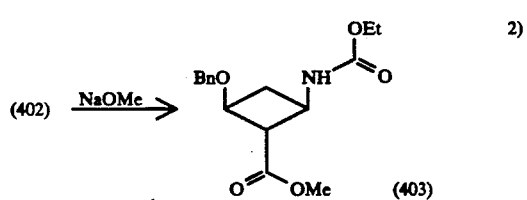

A solution of sodium (31 mg, 1.37 mmols) in dry methanol (5 ml) was added dropwise to a solution of compound (402) (188 mg, 0.68 mmol) in dry methanol (5 ml) at room temperature and this mixture was stirred at room temperature for 2 days.

The solvent was distilled off and the residue was chromatographed on silica gel (10 g) with hexane-ethyl acetate (3:1) to give the product (403) (133 mg, 64%).

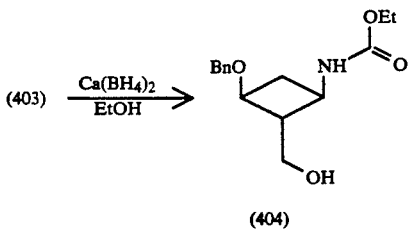

A solution of sodium borohydride (73 mg, 1.94 mmol) in ethanol (5 ml) was added dropwise to a solution of calcium chloride (107 mg, 0.97 mmol) in ethanol (5 ml) in an ice bath and the mixture was stirred for 30 minutes. Next, a solution of compound (403) (119 mg, 0.39 mmol) in ethanol (5 ml) was added to the mixture by small portions. The temperature was gradually raised to room temperature and the reaction was performed for further 19 hours.

The solvent was distilled off and the residue was washed with water and then extracted with ethyl acetate. The extract was dried over sodium sulfate.

The solvent was distilled off and the residue was chromatographed on silica gel (12 g) with hexane-ethyl acetate (1:1) to give the product (404) (50 mg, 46%).

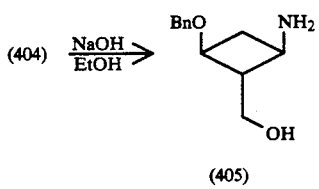

An aqueous 2N sodium hydroxide solution (5 ml) was added to a solution of compound (404) (50 mg, 0.179 mmol) in ethanol (10 ml), and the mixture was refluxed for 3.5 hours.

The solvent was distilled off and the residue was washed with water and then extracted with ethyl acetate. The extract was dried over sodium sulfate. The solvent was distilled off and the residue was developed on thin layer chromatography with an ethyl acetate-hexane solution (3:1), to give product (405) (22 mg, 60%).

EXAMPLE 5

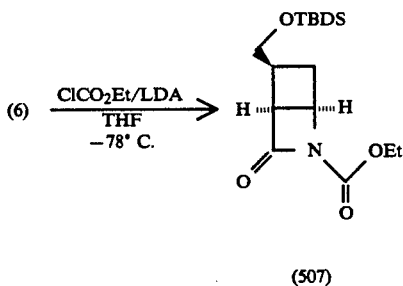

A solution of n-butyl lithium (1.6M in hexane) (4.4 ml, 7.05 mmols) was added to a solution of diisopropylamine (712 mg, 7.05 mmols) in tetrahydrofuran (10 ml) at −78° C. and then the mixture was stirred for thirty minutes. A solution of compound (506) (850 mg, 3.53 mmols) in tetrahydrofuran (10 ml) was added dropwise to the mixture and then the mixture was stirred for 30 minutes. A solution of ethyl chlorocarbonate (761 mg, 7.05 mmols) in tetrahydrofuran (10 ml) was added dropwise to the mixture and then the mixture was stirred at −78° C. for 3 hours. Finally, the temperature was gradually reverted to room temperature and saturated aqueous ammonium chloride solution (10 ml) was added to the mixture followed by vigorous stirring for 30 minutes. The reaction mixture was extracted with ethyl acetate and the extract was dried over sodium sulfate.

The solvent was distilled off and the residue was chromatographed on silica gel (40 g) with ethyl acetate to give the product (507) (305 mg, 28%).

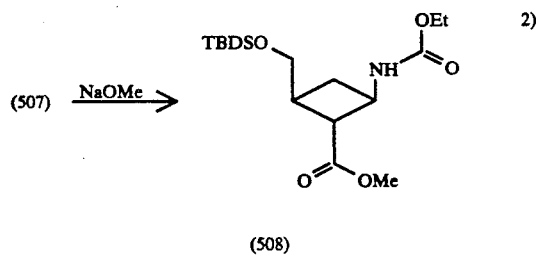

A solution of sodium (33 mg, 1.44 mmol) in dry methanol (5 ml) was dropwise added to a solution of compound (507) (300 mg, 0.96 mmol) in dry methanol (5 ml) at room temperature and then the mixture was stirred for two days.

The solvent was distilled off and the residue was chromatographed on silica gel (15 g) with hexane-ethyl acetate solution (5:1) to give the product (508) (220 mg, 67%).

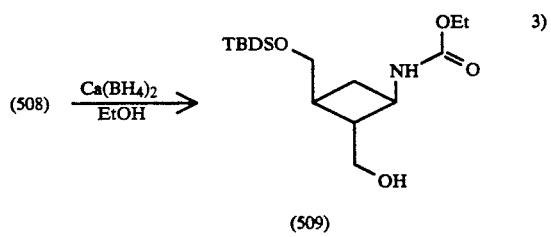

A solution of sodium borohydride (113 mg, 3.0 mmols) in ethanol (5 ml) was added dropwise to a solution of calcium chloride (165 mg, 1.5 mmol) in ethanol (5 ml) in ice bath and the mixture was stirred for 30 minutes. Next, a solution of compound (507) (205 mg, 0.6 mmol) in ethanol (5 ml) was added to the mixture by small portions. The temperature was gradually raised to room temperature and the reaction was performed for further 11.5 hours.

The solvent was distilled off and the residue was washed with water and then extracted with ethyl acetate. The extract was dried over sodium sulfate.

The solvent was distilled off and the residue was chromatographed on silica gel (10 g) with hexane-ethyl acetate solution (2:1) to give the product (509) (151 mg, 80%).

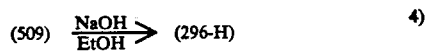

An aqueous 2N sodium hydroxide solution (10 ml) was added to a solution of compound (509) (135 mg, 0.427 mmol) in ethanol (10 ml), and the mixture was refluxed for 3 hours.

The solvent was distilled off and the residue was dissolved in water and then washed with ethyl acetate. The solvent was removed and the resulting residue was distilled under reduced pressure to give compound (29b-H) as light yellow oil.

What is claimed is:

1. A process for producing a cyclobutane derivative represented by the general formula (28):

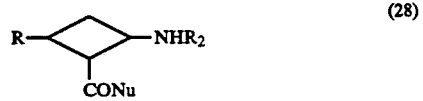
(28)

(wherein R represents a substituent selected from the group consisting of an alkyl group, a hydroxy group which may be protected, and a hydroxymethyl group which may be protected; $R_2$ represents an electron attracting group selected from the group consisting of —CONHR' and —COR", wherein R' is selected from the group consisting of hydrogen, an acyl group, an alkyl group, and an aryl group and R" is selected from the group consisting of an alkyl group, an alkoxy group and a phenyl group and Nu represents a substituent corresponding to a nucleophilic reagent Nu$^\ominus$ selected from the group consisting of an alkoxy group, a cyano group, an amino group, a substituted amino group, a hydroxy group and an acetoxy group) which comprises reacting a compound represented by general formula (27):

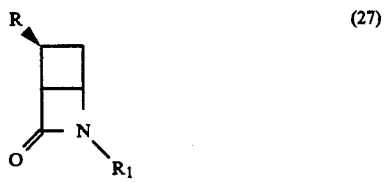
(27)

(wherein R has the same significance as defined above and $R_1$ represents an electron attracting group selected from the group consisting of —CONHR' and —COR", wherein R' is selected from the group consisting of hydrogen, an acyl group, an alkyl group, and an aryl group and R" is selected from the group consisting of an alkyl group, an alkoxy group and a phenyl group) with said nucleophilic reagent Nu$^\ominus$ in a solvent.

2. A process according to claim 1, wherein R is a hydroxy group which may be protected with protecting group or a hydroxymethyl group in which the hydroxy group may be protected with protecting group.

3. A process according to claim 2, wherein protecting group is an alkoxyalkyl ether group, silylether group, substituted methyl ether group, acyl group or carbamoyl group.

4. A process according to claim 1, wherein R is a hydroxy group which may be protected with an alkyl or an aralkyl or a hydroxymethyl group wherein the hydroxy group may be protected with a silyl protective group; $R_1$ and $R_2$ represent —CONHR' (wherein R' is a substituent selected from the group consisting of hydrogen, an acyl group, an alkyl group, and an aryl group) or —COR" (wherein R" is a substituent selected from the group consisting of an alkyl group, an alkoxy group and a phenyl group; and said nucleophilic reagent Nu$^\ominus$ is alkoxide ions.

5. A process according to claim 4, wherein R' is hydrogen or an acyl group and R" is an alkyl group or an alkoxy group.

6. A process according to claim 1, wherein R is a hydroxymethyl group protected with a silyl protective group; $R_1$ is an acylcarbamoyl group or an alkoxycarbonyl group; $R_2$ is an acylcarbamoyl group or an alkoxycarbonyl group; and Nu is an alkoxy group.

7. A process according to claim 6, wherein said hydroxymethyl group is t-butyldimethylsilyloxymethyl group; said acylcarbamoyl group is chloroacetylcarbamoyl group; said alkoxycarbonyl group is ethoxycarbamoyl group; and said alkoxy group is methoxy group.

8. A process according to claim 1, wherein said solvent is an alcohol.

9. A process according to claim 8, wherein said alcohol is methanol.

10. A process for producing a (1β, 2β, 3β) cyclobutane derivative represented by formula (28b):

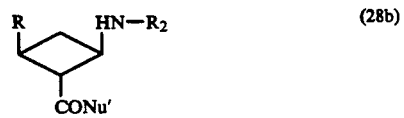
(28b)

(wherein R represents a substituent selected from the group consisting of an alkyl group, a hydroxy group which may be protected, and a hydroxymethyl group which may be protected; $R_2$ represents an electron attracting group selected from the group consisting of —CONHR' and —COR", wherein R' is selected from the group consisting of hydrogen, an acyl group, an alkyl group, and an aryl group and R" is selected from the group consisting of an alkyl group, an alkoxy group and a phenyl group and Nu' represents an alkoxy group) which comprises reacting a compound represented by formula (27):

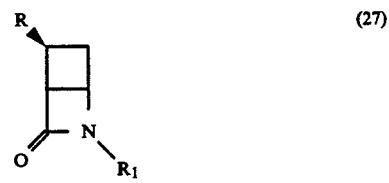
(27)

(wherein R has the same significance as defined above and $R_1$ represents an electron attracting group selected from the group consisting of —CONHR' and —COR", wherein R' is selected from the group consisting of hydrogen, an acyl group, an alkyl group, and an aryl group and R" is selected from the group consisting of an alkyl group, an alkoxy group and a phenyl group) with a metal alkoxide, in an alcohol solvent.

11. A process according to claim 4, wherein $R_2$ represents —CONH$_2$.

12. A process for producing a (1β, 2β, 3β) cyclobutane derivative represented by formula (28b):

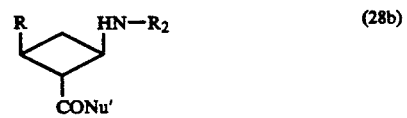
(28b)

(wherein R represents a substituent selected from the group consisting of an alkyl group, a hydroxy group which may be protected, and a hydroxymethyl group which may be protected; $R_2$ represents an electron attracting group selected from the group consisting of —CONHR' and —COR", wherein R' is selected from the group consisting of hydrogen, an acyl group, an alkyl group, and an aryl group and R" is selected from the group consisting of an alkyl group, an alkoxy group and a phenyl group and Nu' represents an alkoxy group) which comprises reacting a compound represented by formula (27):

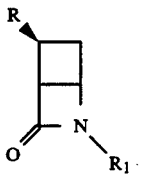 (27)

(wherein R has the same significance as defined above and $R_1$ represents an electron attracting group selected from the group consisting of —CONHR' and —COR", wherein R' is selected from the group consisting of hydrogen, an acyl group, an alkyl group, and an aryl group and R" is selected from the group consisting of an alkyl group, an alkoxy group and a phenyl group) with an alcohol, in the presence of a borohydride compound or a trialkylamine to give a compound represented by formula (28a):

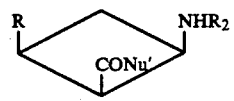 (28a)

(wherein R, $R_2$ and Nu' have the same significances as described above), the steric configuration of which is (1β, 2β, 3β); and then reacting this compound with an alkali metal alkoxide in an alcohol solvent.

* * * * *